United States Patent
Kelly

(10) Patent No.: US 9,095,465 B2
(45) Date of Patent: Aug. 4, 2015

(54) STENT DEPLOYMENT DEVICE AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls (SD)

( * ) Notice: Subject to any disclaimer, the term of this patent is extended or adjusted under 35 U.S.C. 154(b) by 0 days.

(21) Appl. No.: 13/974,626

(22) Filed: Aug. 23, 2013

(65) Prior Publication Data

US 2014/0180381 A1 Jun. 26, 2014

Related U.S. Application Data

(63) Continuation of application No. 13/943,863, filed on Jul. 17, 2013.

(60) Provisional application No. 61/740,161, filed on Dec. 20, 2012, provisional application No. 61/834,014, filed on Jun. 12, 2013.

(51) Int. Cl.
*A61F 2/966* (2013.01)
*A61F 2/95* (2013.01)

(52) U.S. Cl.
CPC ......... *A61F 2/966* (2013.01); *A61F 2002/9517* (2013.01)

(58) Field of Classification Search
CPC ............. A61F 2/94; A61F 2/95; A61F 2/962; A61F 2/966
USPC ............... 606/200; 623/1.11, 1.12, 1.13, 1.14
See application file for complete search history.

(56) References Cited

U.S. PATENT DOCUMENTS

| | | | |
|---|---|---|---|
| 2,722,931 | A | 11/1955 | May |
| 4,474,572 | A | 10/1984 | McNaughton et al. |
| 4,655,771 | A | 4/1987 | Wallsten |
| 5,383,892 | A | 1/1995 | Cardon et al. |
| 5,415,664 | A | 5/1995 | Pinchuk |
| 5,433,723 | A | 7/1995 | Lindenberg et al. |

(Continued)

FOREIGN PATENT DOCUMENTS

| | | |
|---|---|---|
| DE | 10 2010 019045 | 11/2011 |
| EP | 0747021 | 12/1996 |

(Continued)

OTHER PUBLICATIONS

International Search Report for PCT/US03/08436, mailed Mar. 8, 2003.

(Continued)

*Primary Examiner* — Ryan Severson
*Assistant Examiner* — Anh Dang
(74) *Attorney, Agent, or Firm* — McDonnell Boehen Hulbert & Berghoff LLP

(57) ABSTRACT

A stent deployment device and methods for use, where the device comprises: (a) an outer sheath having a proximal end and a distal end, (b) a pull apparatus at least partially disposed within the outer sheath, where a portion of the pull apparatus is sized and shaped to receive a stent or a stent graft, (c) a push apparatus, where a portion of the push apparatus is sized to fit within a portion of the pull apparatus, and (d) a push-pull drive mechanism in mechanical communication with the pull and push apparatuses, where the push-pull drive mechanism includes at least a push and a pull gear or a push and a pull reel sized and shaped based on a stent ratio.

23 Claims, 14 Drawing Sheets

(56) References Cited

U.S. PATENT DOCUMENTS

| | | |
|---|---|---|
| 5,669,880 A | 9/1997 | Solar |
| 5,707,376 A | 1/1998 | Kavteladze et al. |
| 5,776,140 A | 7/1998 | Cottone |
| 5,968,052 A | 10/1999 | Sullivan, III et al. |
| 6,019,778 A | 2/2000 | Wilson et al. |
| 6,143,021 A | 11/2000 | Staehle |
| 6,190,393 B1 | 2/2001 | Bevier et al. |
| 6,270,521 B1 | 8/2001 | Fischell et al. |
| 6,371,963 B1 | 4/2002 | Nishtala et al. |
| 6,402,760 B1 | 6/2002 | Fedida |
| 6,425,898 B1 | 7/2002 | Wilson et al. |
| 6,527,779 B1 | 3/2003 | Rourke |
| 6,613,075 B1 | 9/2003 | Healy et al. |
| 6,736,840 B2 | 5/2004 | Fischell et al. |
| 6,743,219 B1 | 6/2004 | Dwyer et al. |
| 6,773,446 B1 | 8/2004 | Dwyer et al. |
| 7,052,511 B2 | 5/2006 | Weldon et al. |
| 7,169,170 B2 | 1/2007 | Widenhouse |
| 7,175,650 B2 | 2/2007 | Ruetsch |
| 7,837,725 B2 | 11/2010 | Fitzgerald et al. |
| 7,850,724 B2 | 12/2010 | Oliver |
| 8,057,529 B2 | 11/2011 | Cox et al. |
| 8,167,892 B2 | 5/2012 | Feller, III et al. |
| 8,257,420 B2 | 9/2012 | Fitzgerald et al. |
| 8,323,327 B2 | 12/2012 | Bei et al. |
| 2004/0127912 A1 | 7/2004 | Rabkin et al. |
| 2007/0123971 A1 | 5/2007 | Kennedy, II et al. |
| 2007/0191925 A1 | 8/2007 | Dorn |
| 2008/0097572 A1 | 4/2008 | Sheldon et al. |
| 2011/0034987 A1 | 2/2011 | Kennedy |
| 2011/0295354 A1 | 12/2011 | Bueche et al. |
| 2012/0065644 A1 | 3/2012 | Ng et al. |
| 2012/0172963 A1 | 7/2012 | Ryan |
| 2013/0226276 A1* | 8/2013 | Newell et al. ............... 623/1.11 |

FOREIGN PATENT DOCUMENTS

| | | |
|---|---|---|
| EP | 1078611 | 2/2001 |
| EP | 1494620 | 12/2006 |
| GB | 757405 | 9/1956 |
| WO | 00/18330 | 4/2000 |
| WO | 02/03888 | 1/2002 |
| WO | 03/084439 | 10/2003 |

OTHER PUBLICATIONS

International Search Report and Written Opinion for PCT/US2013/076942 mailed Apr. 4, 2014.
International Search Report and Written Opinion for PCT/US2014/053149 mailed Nov. 19, 2014.

* cited by examiner

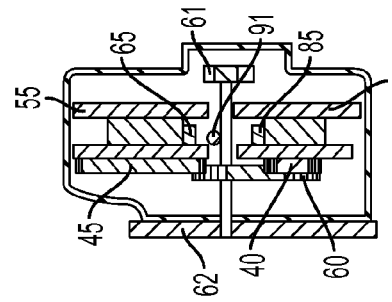
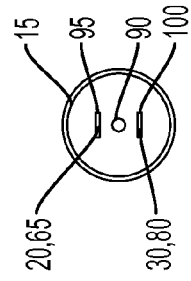
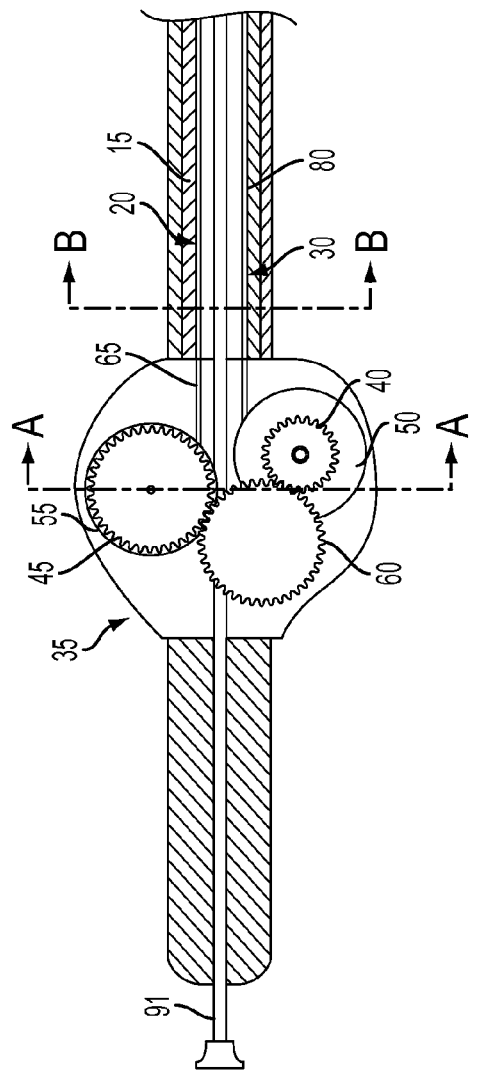

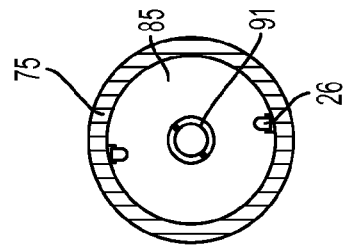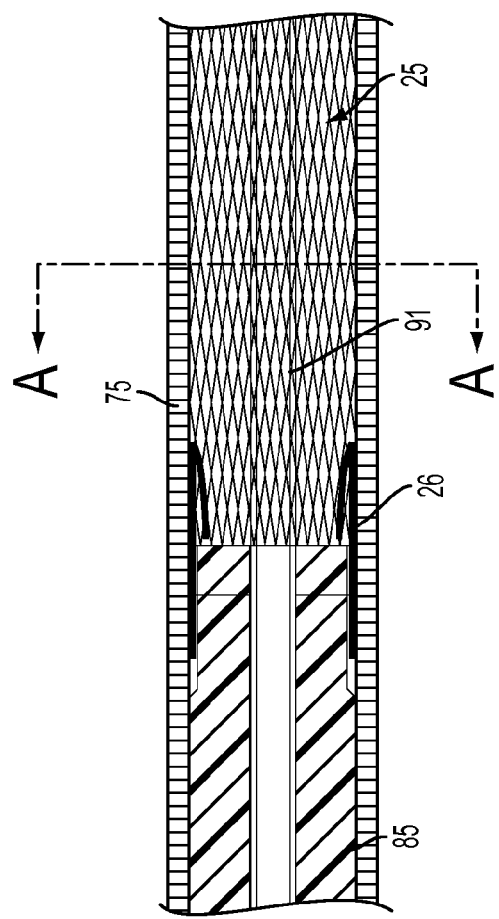

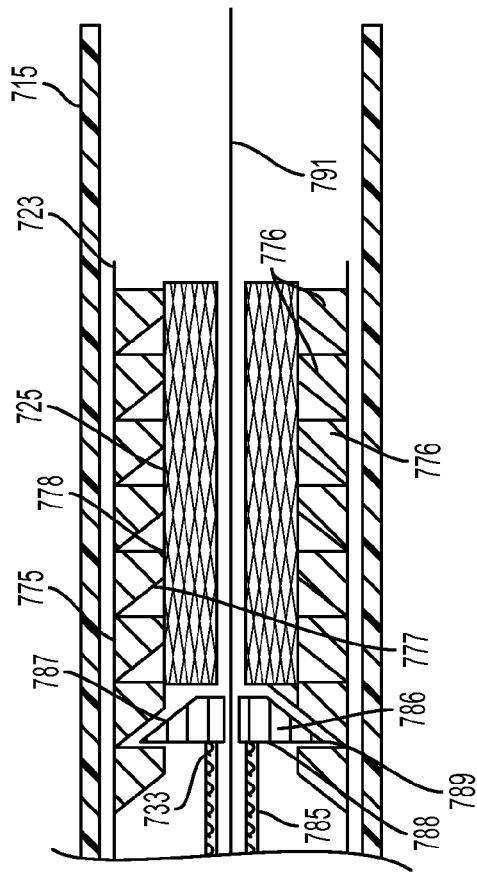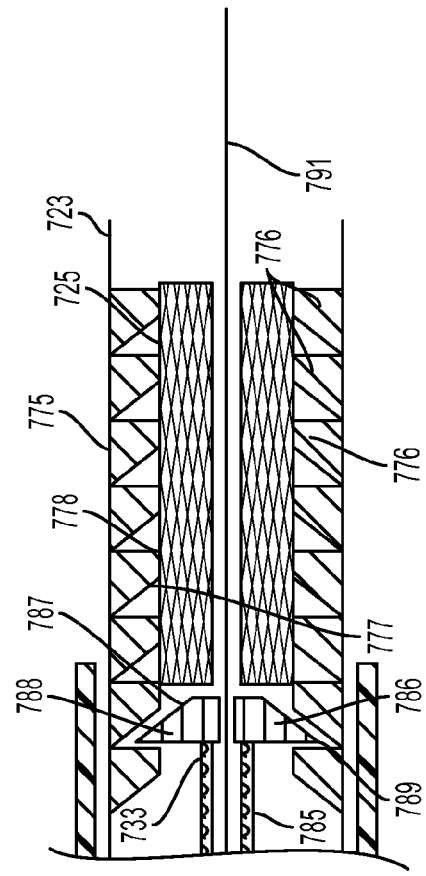
FIG. 7A
FIG. 7B

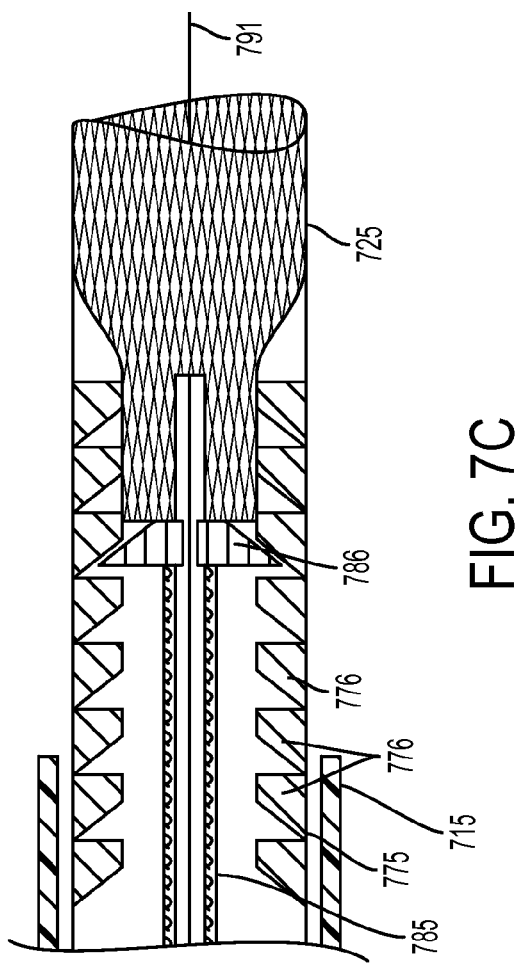
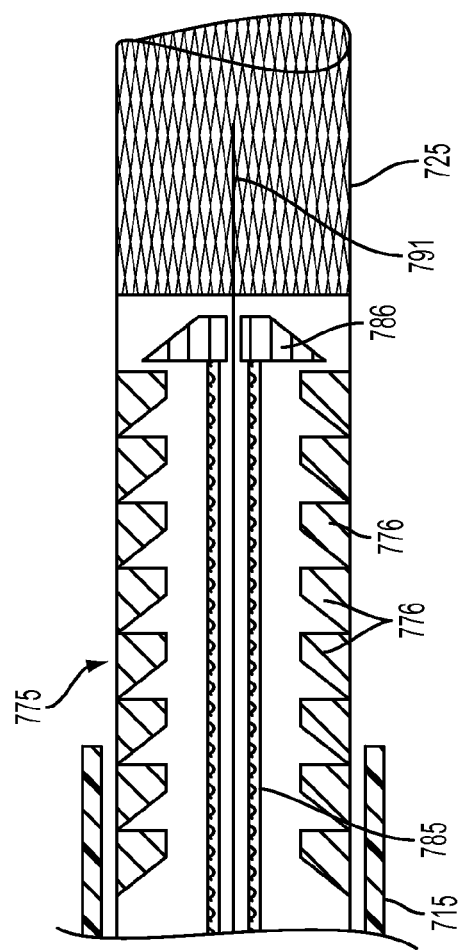

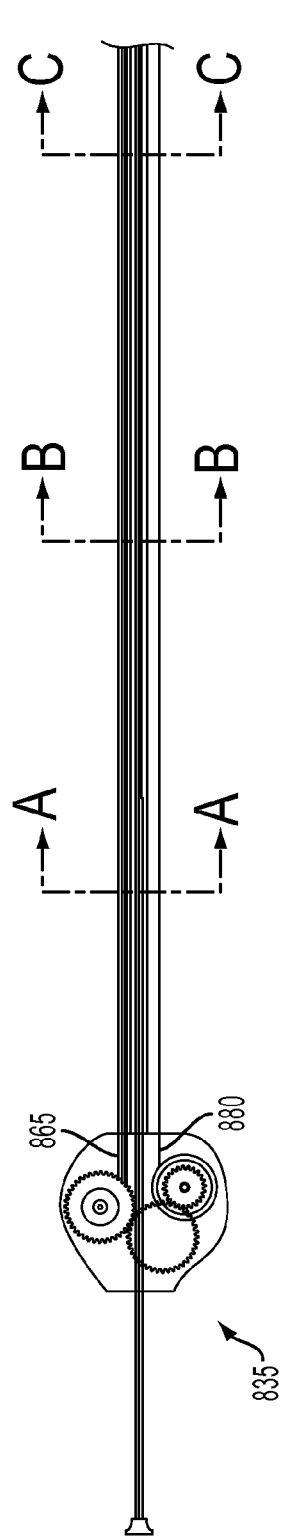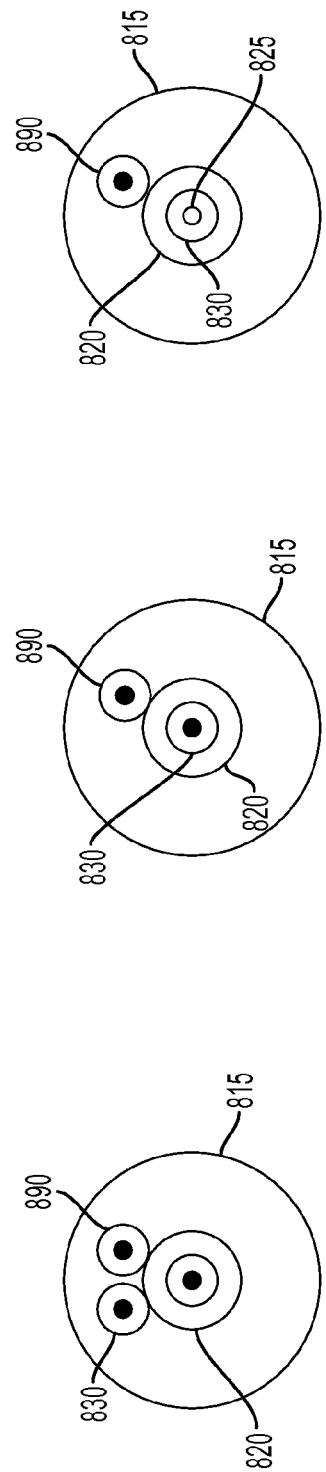

STENT DEPLOYMENT DEVICE AND METHODS FOR USE

RELATED APPLICATIONS

This application is a continuation application of and claims priority to U.S. Non-Provisional application Ser. No. 13/943,863 entitled "Stent Deployment Device and Methods for Use," filed Jul. 17, 2013, which in turn claims priority to U.S. Provisional Application No. 61/740,161 entitled "Stent Deployment Device," filed Dec. 20, 2012 and to U.S. Provisional Application No. 61/834,014 entitled "Stent Deployment Device," filed Jun. 12, 2013, which are hereby incorporated by reference in their entirety.

BACKGROUND OF THE INVENTION

Stent deployment devices are utilized to direct the placement of a stent in a human or animal body and to ultimately eject and deploy a stent in a targeted lumen. Conventional stent deployment methods and devices can only be used with stents, as opposed to stent grafts. This is because known stent restraint mechanisms that prevent premature deployment must physically interact with the stent wires. This interaction is not possible with a stent graft because the graft covering prevents the stent restraint from locking onto the wireframe of a stent graft.

In addition, a stent often has a constrained, compressed length that is much longer than its unconstrained, expanded length. These customary methods and devices deploy stents in a manner that moves the stent in a back-and-forth motion. This results in the stent structure making delayed contact with the target lumen's wall and the stents become elongated in vivo.

SUMMARY OF THE INVENTION

The present invention provides a stent deployment device that is capable of deploying either a stent or a stent graft based on a stent ratio such that contact with the target lumen's wall is not delayed and in some embodiments may optionally result in packing the stent or stent graft in the target lumen. This capability allows the stent deployment device to deploy a stent or stent graft in a more reliable manner with respect to stent positioning and stent fixation within the target lumen. In one embodiment, the stent deployment device has the additional benefit of having a stent restraint that allows the device to recapture a compatible stent or woven stent graft, such that the device is capable of pulling a partially deployed stent back into the deployment device. Notably, the stent restraint is effective to recapture a stent that has up to 90% of its length deployed in a target lumen. The stent or stent graft may then be released once the desired positioning is achieved. The present invention further provides methods for use of the stent deployment device.

Thus, in a first aspect, the present invention provides a stent deployment device comprising: (a) an outer sheath, where the outer sheath has a proximal end and a distal end, (b) a pull apparatus at least partially disposed within the outer sheath, where a portion of the pull apparatus is sized and shaped to receive a stent or a stent graft, (c) a push apparatus, where a portion of the push apparatus is sized to fit within a portion of the pull apparatus, and (d) a push-pull drive mechanism in mechanical communication with the pull apparatus and the push apparatus, where the push-pull drive mechanism includes at least a push gear and a pull gear or a push reel and a pull reel that are sized and shaped based on a stent ratio.

In one embodiment, the invention provides that the push-pull drive mechanism comprises: (a) a pull reel coupled to a proximal end of the pull apparatus, (b) a pull gear in mechanical communication with the pull reel, (c) a push reel coupled to a proximal end of the push apparatus, (d) a push gear in mechanical communication with the push reel, and (e) a drive gear in mechanical communication with the push gear and the pull gear, where the push gear and the pull gear are sized and shaped based on the stent ratio.

In another embodiment, the invention provides that the push-pull drive mechanism comprises: (a) the pull reel, (b) the push reel, where the push reel and the pull reel are sized and shaped based on the stent ratio, and (c) a drive gear, where the pull reel, the push reel and the drive gear are coupled together along a shared axis.

In still a further embodiment, the invention provides that the push-pull drive mechanism comprises: (a) a push rack coupled to the push apparatus, where the push rack defines a plurality of teeth, (b) a push pinion engaged with at least one tooth of the plurality of teeth of the push rack, (c) the push gear coupled to the push pinion, (d) a pull rack coupled to the pull apparatus, where the pull rack defines a plurality of teeth, (e) a pull pinion engaged with at least one tooth of the plurality of teeth of the pull rack, (f) the pull gear coupled to the pull pinion, and (g) a drive gear coupled to both the push gear and the pull gear, where the push gear and the pull gear are sized and shaped based on the stent ratio.

In a second aspect, the present invention also provides a method for placement of a stent graft comprising: (a) simultaneously advancing a stent or a stent graft distally with a push apparatus of a stent deployment device and retracting a pull apparatus of the stent deployment device proximally at two different rates based on a stent ratio, and (b) deploying the stent or the stent graft into a lumen.

BRIEF DESCRIPTION OF THE DRAWINGS

FIG. 2A is detail view A of FIG. 1 showing a cross-section of the push-pull drive mechanism and a portion of an outer sheath, a push apparatus and a pull apparatus according to one embodiment.

FIG. 2A-A is a cross-sectional front view of an example push-pull drive mechanism.

FIG. 2A B-B is a cross-sectional front view of a portion of the outer sheath, the push apparatus and the pull apparatus in a first region of the device.

FIG. 2B A-A is a cross-sectional front view of a portion of the outer sheath, the pull apparatus and the push apparatus in a second region of the device.

FIG. 2B-B is a cross-sectional front view of a portion of the outer sheath, the pull apparatus and the push apparatus in a third region of the device.

FIG. 2C is detail view C of FIG. 1 showing a cross-section of a portion of the outer sheath, the pull apparatus and the push apparatus according to one embodiment.

FIG. 2C A-A is a cross-sectional front view of a portion of the outer sheath, the pull apparatus and the push apparatus in a fourth region of the device.

FIG. 7A is a side view of the pull apparatus, the push apparatus and a stopper wedge at a first time T1 prior to deployment.

FIG. 7B is a side view of the pull apparatus, the push apparatus and a stopper wedge at a second time T2 with the pull apparatus partially retracted.

FIG. 7C is a side view of the pull apparatus, the push apparatus and the stopper wedge at a third time T3 with the stent partially deployed.

FIG. 7D is a side view of the pull apparatus, the push apparatus and the stopper wedge at a fourth time T4 with the stent fully deployed.

FIG. 8 is a side cross-sectional view according to an embodiment utilizing a three-tube manifold.

FIG. 8 A-A shows a front cross-sectional view of a portion of an outer sheath, a pull wire lumen, a push wire lumen and a guidewire lumen according to one embodiment in a first region.

FIG. 8 B-B shows a front cross-sectional view of a portion of the outer sheath, the pull apparatus, the push apparatus and the guidewire lumen according to one embodiment in a second region.

FIG. 8 C-C shows a front cross-sectional view of a portion of the outer sheath, the pull apparatus, the push apparatus and the guidewire lumen according to one embodiment in a third region.

DETAILED DESCRIPTION OF THE INVENTION

Figure 1:
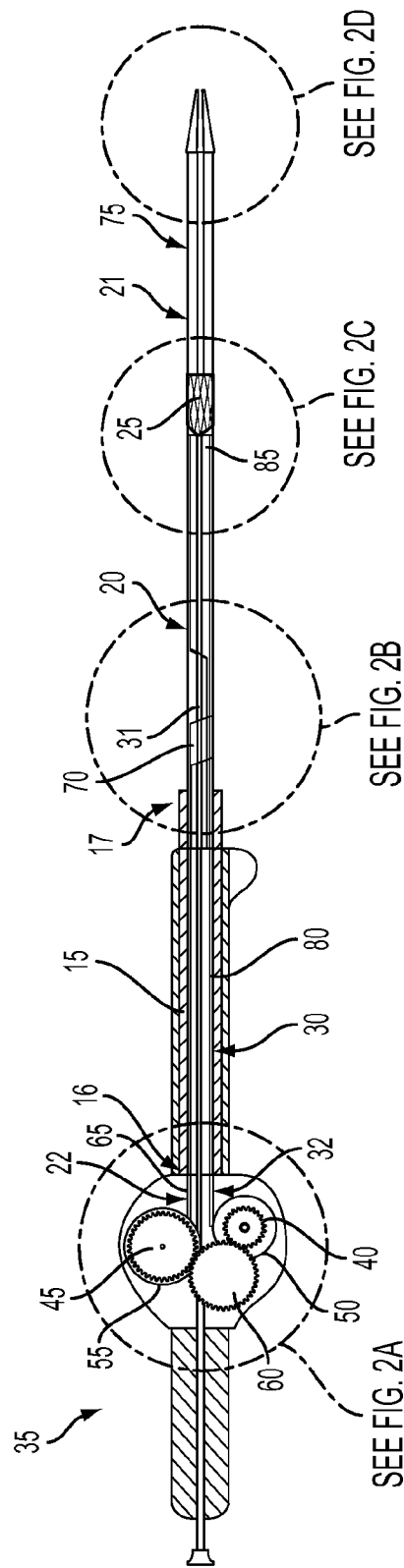
FIG. 1 is a cross-sectional side view of the stent deployment device in accordance with one embodiment of the invention.
Figure 2B:
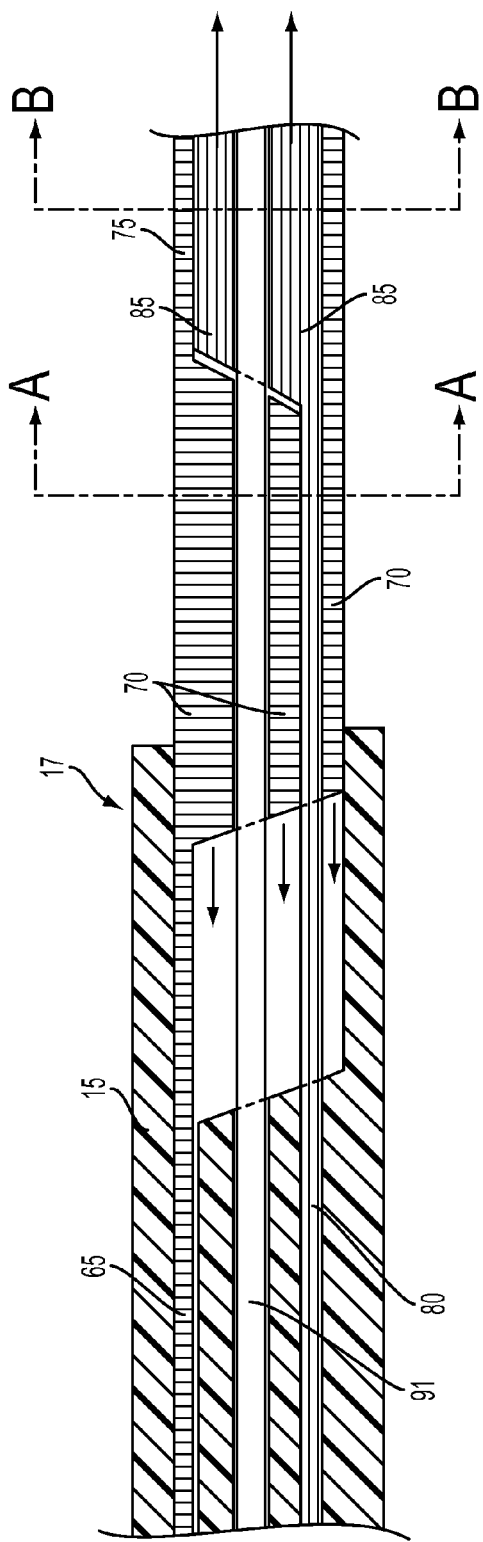
FIG. 2B is detail view B of FIG. 1 showing a cross-section of a portion of the outer sheath, the pull apparatus and the push apparatus according to one embodiment.
Figure 2B:
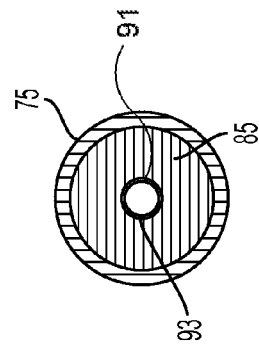
Figure 2B:
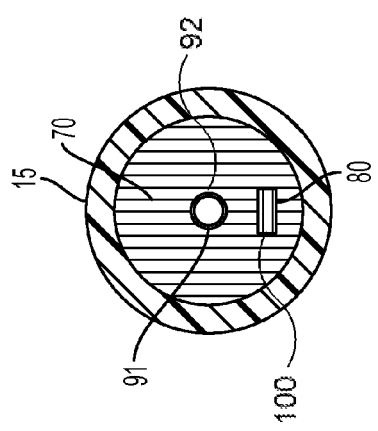
Figure 2D:
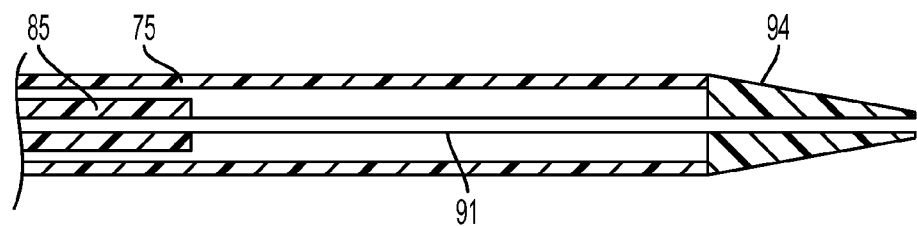
FIG. 2D is detail view D of FIG. 1 showing a cross-section of a guidewire and a nose cone according to one embodiment.

In a first aspect, as shown in FIGS. 1 and 2A-D, 4, 5A-B and 6A-B, the present invention may take the form of a stent deployment device 10 comprising: (a) an outer sheath 15, where the outer sheath 15 has a proximal end 16 and a distal end 17, (b) a pull apparatus 20 at least partially disposed within the outer sheath 15, where a portion 21 of the pull apparatus 20 is sized and shaped to receive a stent or a stent graft 25, (c) a push apparatus 30, where a portion 31 of the push apparatus 30 is sized to fit within the pull apparatus 20, and (d) a push-pull drive mechanism 35 in mechanical communication with the pull apparatus 20 and the push apparatus 30, where the push-pull drive mechanism 35 includes at least a push gear 40 and a pull gear 45 or a push reel 50 and a pull reel 55 that are sized and shaped based on a stent ratio.

As used herein, with respect to measurements and calculations, "about" means +/−5%.

As used herein, "stent" is used broadly to refer to both stents and stent grafts 25. The stent or stent graft 25 is self-expandable. As used herein, "stent" is typically a cylindrical frame and means any device or structure that adds rigidity, expansion force, or support to a prosthesis or native vasculature, while "stent graft" refers to a prosthesis comprising a stent and a graft material associated therewith that forms a fluid-tight lumen through at least a portion of its length. For example, the stent structure may comprise coiled, mesh, zig zag, braided, knitted or woven wires. The stent structure could also comprise a laser cut sheet or a laser cut tube that may have various lengths, diameters or wall thickness. Alternatively, the stent may comprise injection molded metal. A "graft" is a cylindrical liner that may be disposed on the stent's interior, exterior or both. Further, when used in combination with a graft, the stent structure may further comprise a series of spaced apart stent rings disposed along the graft. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality nitinol, cobalt chromium, stainless steel wires, nickel and titanium alloys, and biocompatible plastics attached to a graft. Any suitable fluid tight graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

The covered stent grafts can be made of any suitable material, including but not limited to polytetrafluoroethylene (ePTFE) lined nickel-titanium alloy stent. The stent grafts are preferably covered and flexible. The stent grafts may contain any other suitable components, such as surface modifications including but not limited to covalent attachment of heparin.

Figure 3:
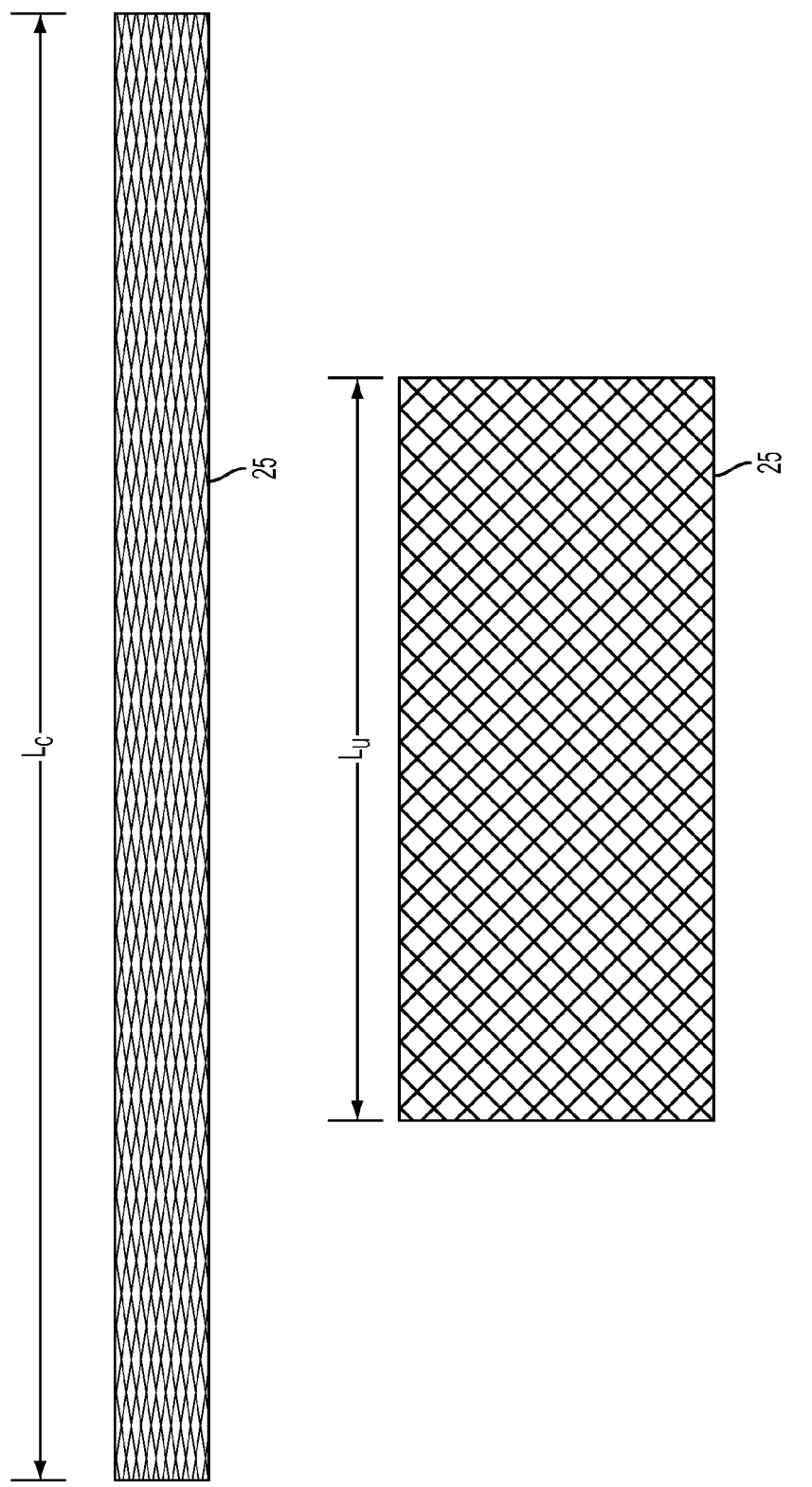
FIG. 3 is a side view showing an example configuration of an unconstrained length $L_u$ of a to-be-deployed stent or stent graft and a constrained length $L_c$ of the stent or stent graft.

As shown in FIG. 3, stent 25 has unconstrained, expanded length $L_u$ and a constrained, compressed length $L_c$. The unconstrained length $L_u$ of the stents or stent grafts 25 may range from about 40 mm to about 200 mm and, in various embodiments, may be between about 40-180 mm, 40-160 mm, 40-140 mm, 40-120 mm, 40-100 mm, 40-80 mm, 40-60 mm, 60-200 mm, 80-200 mm, 100-200 mm, 120-200 mm, 140-200 mm, 160-200 mm, 180-200 mm, 40 mm, 60 mm, 80 mm, 120 mm or 200 mm. The constrained length $L_c$ of the stent 25 is a factor of the stent's unconstrained diameter, the length of the unconstrained stent, the weave pattern of a woven stent and the size of the French sheath into which the stent is to be constrained.

As used herein, the "stent ratio" is equal to a ratio of a quantity of the constrained length $L_c$ of a to-be-deployed stent 25 less an unconstrained length $L_u$ of the stent 25 to the unconstrained length $L_u$ of the stent 25 and is defined based on the following relationship:

$$\phi_g = \frac{L_c - L_u}{L_u}$$

In various embodiments, in which either the pull reel and the push reel diameters are the same size or in the absence of the push and pull reels, Ø$_g$: ratio of pull gear diameter to push gear diameter
L$_c$: length of a constrained stent
L$_u$: length of an unconstrained stent.

For example, if a stent has an unconstrained length of 40 cm and a constrained length of 100 cm, then the stent ratio is (100 cm−40 cm)/40 cm or 1.5. Thus, in this example, the pull gear will have a diameter 1.5 times larger than the diameter of the push gear such that the push shaft will advance at a faster rate than the rate that the pull apparatus is retracted.

In various alternative embodiments, in which either the pull gear and push gear diameters are the same size, the pull reel and push reel share a single axis with a drive gear or in the absence of the push and pull gears, the stent ratio is defined as:

$$\phi_r = \frac{L_c - L_u}{L_u}$$

Ø$_r$: ratio of push reel diameter to pull reel diameter
L$_c$: length of a constrained stent
L$_u$: length of an unconstrained stent.

For example, if a stent has an unconstrained length of 40 cm and a constrained length of 100 cm, the stent ratio will be 1.5 and the push reel will have a diameter 1.5 times larger than the diameter of the pull reel. In another example, if the constrained length of the stent is 100 cm and the unconstrained length is 60 cm, then the stent ratio is (100 cm−60 cm)/60 cm or 2/3. In this example, the push reel diameter is 2/3 the size of the pull reel diameter and the push shaft will advance at a rate slower than the pull apparatus is retracted. In various alternative embodiments, many other gear and reel combinations may achieve the "stent ratio" through proper sizing based on accepted machine design concepts.

The stent ratio may range from about 0 to about 5 and, in various embodiments, may be between about 0 to 0.375, 0 to 0.6251, 0 to 1.5, 0 to 1.75, 0 to 2, 0 to 2.25, 0 to 2.5, 0 to 2.75, 0 to 3, 0 to 3.25, 0 to 3.5, 0 to 3.75, 0 to 4, 0 to 4.25, 0 to 4.5, 0 to 4.75, 0 to 5, 4.75 to 5, 4.5 to 5, 4.25 to 5, 4 to 5, 3.75 to 5, 3.5 to 5, 3.25 to 5, 3 to 5, 2.75 to 5, 2.5 to 5, 2.25 to 5, 2 to 5, 1.75 to 5, 1.5 to 5, 1.25 to 5, 1 to 5, 0.75 to 5, 0.5 to 5, 0.25 to 5, 0, 1, 2, 3, 4 or 5. Note that a stent comprising a laser cut nitinol tube, for example, will have substantially the same unconstrained length and constrained length and a corresponding stent ratio of zero.

In additional embodiments, the "stent" may also include septal, patent foramen ovale or percutaneous, transcatheter occluders or self-expanding valves, such as the Corevalve® manufactured by Medtronic, that each have a constrained and an unconstrained length.

Further, in various embodiments, it may be desirable to "pack" the stent into the vessel in which the stent is being deployed such that the stent is 5-15% shorter than the original unconstrained length. Stent "packing" is desirable because it causes the stent to apply additional radial force to the vessel. Stent "packing" is achieved by applying additional force via the push shaft during deployment by modifying the ratio of the push gear diameter to the pull gear diameter or the ratio of the push reel diameter to the pull reel diameter. Specifically, in one embodiment, a ratio of the push gear diameter to the pull gear diameter is equal to the stent ratio plus 5-15% of the stent ratio. In a preferred embodiment, the ratio of the push gear diameter to the pull gear diameter is equal to the stent ratio plus 10% of the stent ratio. In another embodiment, a ratio of the push reel diameter to the pull reel diameter is equal to the stent ratio plus 5-15% of the stent ratio. In a further preferred embodiment, the ratio of the push reel diameter to the pull reel diameter is equal to the stent ratio plus 10% of the stent ratio.

In one embodiment, shown in FIGS. 1 and 2A-D, the invention provides that the push-pull drive mechanism 35 comprises: (a) a pull reel 55 coupled to a proximal end 22 of the pull apparatus 20, (b) a pull gear 45 in mechanical communication with the pull reel 55, (c) a push reel 50 coupled to a proximal end 32 of the push apparatus 30, (d) a push gear 40 in mechanical communication with the push reel 50, and (e) a drive gear 60 in mechanical communication with the push gear 40 and the pull gear 45, where the push gear 40 and the pull gear 45 are sized and shaped based on the stent ratio.

In one push-pull coil system embodiment, shown in FIG. 2A B-B, at least a portion of the outer sheath 15 defines (i) a central core 90 for receiving a guidewire 91, (ii) a channel 95 for receiving the pull ribbon 65, and (iii) a channel 100 for receiving the push ribbon 80. In addition, the pull apparatus 20 may comprise a ribbon 65 at its proximal end 22 that transitions to a pull shaft 70 and the pull shaft 70 then transitions to a pull tube 75 at the distal end 23 of the pull apparatus 20. The pull shaft 70 may define a pull central core 92 for receiving a guidewire 91 and may further define a channel 100 for receiving the push ribbon 80. In an additional embodiment, the pull apparatus 20 may further comprise a series of sheaths capable of telescoping in a direction distal from the outer sheath 15. The push apparatus 30 may comprise a ribbon 80 at its proximal end 32 that transitions to a push shaft 85 at the distal end 33 of the push apparatus 30. The push shaft 85 has a distal end 33 configured to engage in facial contact with an end of the to-be-deployed stent 25. Alternatively, the push shaft 85 may include a stent restraint 26, discussed in more detail below, that interfaces with the to-be-deployed stent 25. The push shaft 85 may further define a push central core 93 for receiving a guidewire 91. In a further embodiment, the stent deployment device 10 may include a guidewire 91 disposed within the outer sheath central core 90, the pull central core 92 and the push central core 93. In still another embodiment, the stent deployment device 10 may include a stent or a stent graft 25 positioned within the pull tube 75.

In one embodiment, the outer sheath 15, the pull apparatus 20 and the push apparatus 30 are constructed from a stiff, non-kinkable material such as nitinol, a nitinol alloy, polyimide or a hypotube comprising nickel-titanium alloy. As used herein, "non-kinkable" means that the material does not twist, curl, or double over or bend back upon itself. In various other embodiments in which the pull apparatus and the push apparatus define a ribbon portion, the ribbon portions may be contained in narrow ribbon channels in the outer sheath and/or in the pull apparatus that prevent kinking and therefore bending stiffness is not a significant factor. Further, in some embodiments, the outer sheath 15, pull apparatus 20 and the push apparatus 30 each preferably have a hydrophilic coating for a smooth in vivo deployment or another similar non-stick, low-friction surface coating or lubricant, like Polytetrafluoroethylene (PTFE) or Teflon®. Specifically, (a) the outer sheath 15 has a hydrophilic coating disposed on inner surfaces configured to interface with the pull apparatus 20, the push apparatus 30 and a guidewire 91, (b) the pull apparatus 20 has a hydrophilic coating disposed on an outer surface configured to interface with the outer sheath 15 and on inner surfaces configured to interface with the push apparatus 30, a stent 25 and a guidewire 91, and (c) the push apparatus 30 has a hydrophilic coating disposed on outer surfaces configured to interface with the outer sheath 15 and the pull apparatus 20 and on an inner surface configured to interface with a guidewire 91. In addition, the surfaces of the pull apparatus and the push apparatus that are exposed to bodily fluids in vivo are preferably hydrophobic. The outer sheath 15 and/or handle housing 437,438 may comprise a different material on its outer surface that may be gripped by the operator with a frictional, non-slip engagement, such as comprise acrylonitrile butadiene styrene (ABS) plastic, polycarbonate, Delrin® acetal resin (available from DuPont) or rubber, for example. The gear block may also be made out of Delrin acetal resin in some embodiments.

The length of the push shaft 85 preferably is at least as long as the constrained stent 25. The length of the pull tube 75 preferably is long enough to receive both the push shaft 85 and the constrained stent 25. In various embodiments, it is preferred that a to-be-deployed stent be disposed at the distal end of the pull tube 75 to effect the shortest path of travel for both the pull tube 75 and the push shaft 85 during stent deployment. In certain embodiments, the outer diameter of the outer sheath 15 is 5 Fr (0.066 inches; 1.67 mm) or 4 Fr (0.053 inches; 1.33 mm). Other outer diameters of the outer sheath 15 are also possible. In various other embodiments, the outer diameter of the outer sheath 15 is sized to fit within a 6 Fr sheath (0.079 inches; 2.0 mm) or within a 7 Fr sheath (0.092 inches; 2.3 mm).

In one embodiment, the pull sheath may include a radiopaque marker disposed halfway between the distal end of the pull tube 75 and the distal end of the push shaft prior to deployment. In operation, a user would center the radiopaque marker in the middle of a targeted lesion, for example, and then deploy the stent. In an alternative embodiment, the pull sheath may include a radiopaque marker disposed on the distal end of the pull tube 75. In operation, a user would align the radiopaque marker at the end of a targeted lesion, for example, and then deploy the stent.

The "central core" is a channel for receiving a central core guidewire 91. The outer sheath central core 90, the pull central core 92 and the push central core 93 are all aligned in series to receive the central core guidewire 91. In a preferred embodiment, the central core guidewire 91 comprises a flexible spiral tube made of nitinol or a nitinol alloy, for example. The central core guidewire 91 preferably has a hydrophilic coating or another similar non-stick, low-friction surface coating or lubricant for a smooth in vivo deployment. The super-elastic nitinol or nitinol alloy resists kinks to maintain device integrity and retains shape for consistent reliability through procedure. The diameter of the central core guidewire 91 may range from about 0.014 inches to about 0.038 inches, and is preferably about 0.014 inches or about 0.018 inches. The length of the central core guidewire 91 may range from about 80 cm to about 260 cm. The central core guidewire 91 may optionally include tungsten in a polyurethane jacket to enhance radiopacity for better visibility during the procedure.

In operation, in one embodiment in which the pull gear 45 is mounted above the push gear 40, for example, the pull ribbon 65 is wound onto the pull reel 55 from the bottom of the pull reel 55, whereas the push ribbon 80 unwinds from the top of the push reel 50. A drive gear 60 is coupled to both the push gear 40 and the pull gear 45 such that when the drive gear 60 is driven by hand or by motor 61, the push gear 40 and the pull gear 45 turn in the same direction, but the orientation of the push gear 40 and pull gear 45 relative to each other and to the drive gear 60 causes the push ribbon 80 to be unwound and advanced forward and the pull ribbon 65 to be wound and retracted. As noted above, in one embodiment, the drive gear 60 is coupled to a forward-reverse motor 61, for example. In another embodiment, the drive gear 60 may be coupled to a manual override. The manual override comprises a thumb wheel 62. Alternatively, the drive gear 60 itself may be configured to be manually turned by hand. In one embodiment, a drive gear 60 may be in mechanical communication with both the push gear 40 and the pull gear 45 such that when the drive gear 60 is driven by hand or by motor 61, the push gear 40 and the pull gear 45 turn in the same direction. In this example, the orientation of the gears causes the push ribbon 80 to be unwound and advanced forward and the pull ribbon 65 to be wound and retracted.

In the embodiment shown in FIGS. 1 and 2A, the push gear 40 and the pull gear 45 are sized based on the stent ratio. Here, the push gear is smaller than the pull gear. In alternative embodiments, the push reel and the pull reel are sized based on the stent ratio and the push reel is larger than the pull reel.

In a further embodiment, the stent deployment device 10 may include a stent restraint 26. In one embodiment, the stent restraint may comprise a releasable hook system, as shown in FIG. 2C. The hooks interlock with the weavings, coils or struts, for example, of the stent structure. In some embodiments, the stent graft may have one or more uncovered struts at the end of the stent. In a preferred embodiment, hooks are attached to one end of recapture wires, while the other end of the wires is connected to the push apparatus 30. The recapture wires are outwardly biased towards the pull apparatus 20 providing a smooth transition for the stent 25 to be released from the hooks when the stent restraint 26 exits the distal end of the pull apparatus 20. This configuration allows the stent 25 to be recaptured after partial deployment outside the stent device in the target lumen. In other words, the entire stent 25 may be drawn back into the pull tube 75 and/or outer sheath 15 and redeployed and positioned in the lumen. This arrangement permits spontaneous release of the stent from the stent restraint 26 once the stent expands at a distal end to a diameter larger than the radial reach of the recapture wires. The length of the recapture wires is long enough to create a smooth transition from the distal end of the deployment device into the target lumen for stent release. The stent restraint 26 preferably has a minimum of two opposed wire hooks in contact with the stent 25 to avoid creating eccentricity. In an alternative embodiment, the stent restraint 26 may comprise a shape memory nitinol metal, for example, that is hook shaped at room temperature and straightens out at body temperature.

Figure 4A:
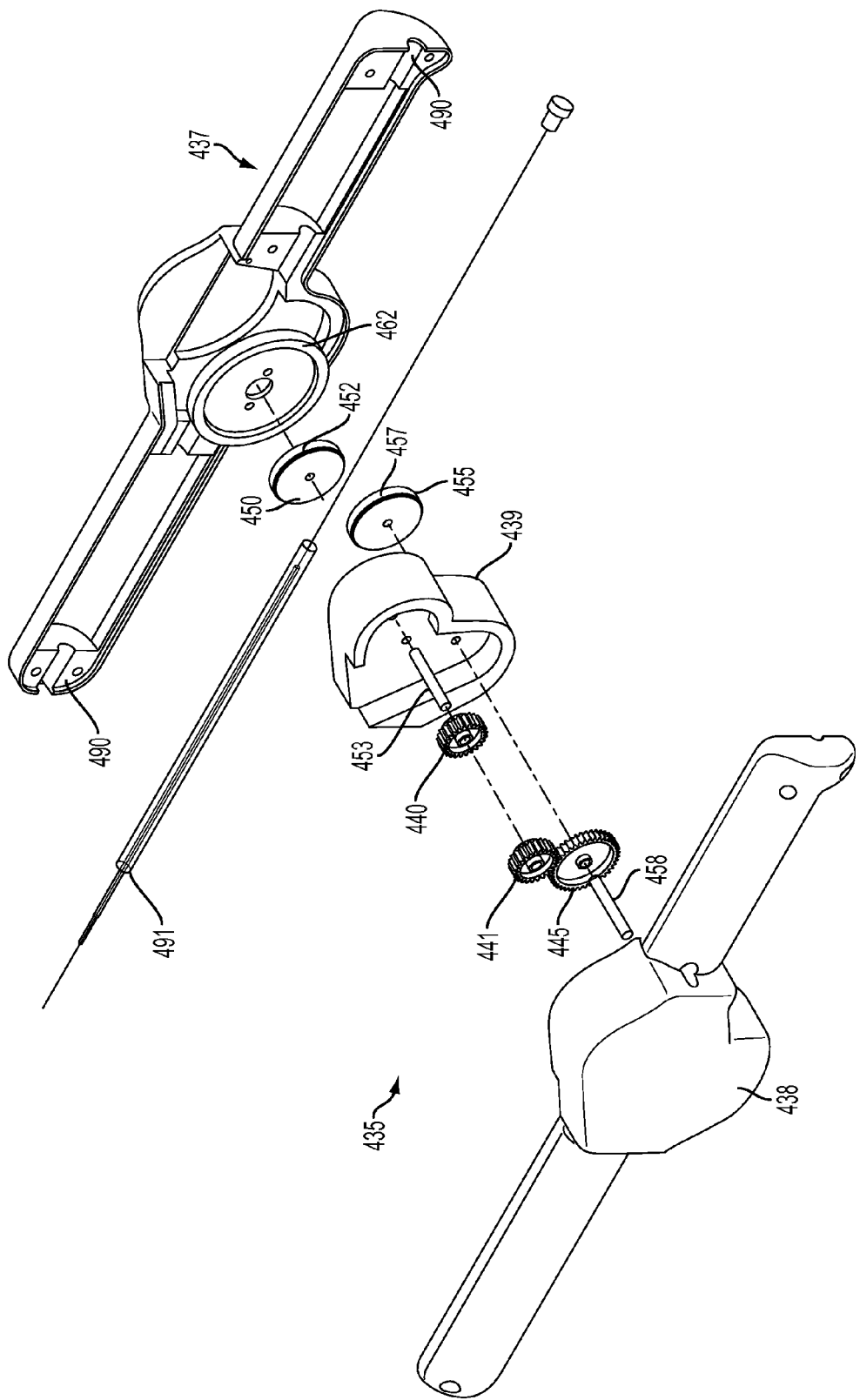
FIG. 4A is an exploded isometric view of the push-pull drive mechanism and a handle housing of the stent deployment device in accordance with one embodiment of the invention.

FIGS. 4A-5B, illustrate another example arrangement of the push-pull drive mechanism 435. Specifically, FIG. 4A shows a thumbwheel 462 intended to be in facial contact with the push reel 450. The push reel 450 shows an optional notch 452 that aids in tangential loading and alignment of the push ribbon with the push reel 450. A connection mechanism, in this example a dowel 453, is disposed within and extends on either side of a gear block 439 and is press fit, for example, into the push reel 450 on one end and fixed at the other end to the push gear 440 via a set screw, for example. The push gear 440 is in mechanical communication with the pull gear 445, which is disposed below the push gear in the gear block 439. In the embodiment shown, the push gear 440 is mated with a translational gear 441, and the translational gear 441 is in turn mated with the pull gear 445. The purpose of the translational gear 441 in this embodiment is to cause the push gear 440 to rotate in the same direction as the pull gear 445. A connection mechanism, in this example a dowel 458, is disposed within and extends on either side of the gear block 439. The pull gear 445 is fixed to one end of the dowel 458 via a set screw, for example, and a pull reel 455 is press fit, for example, to the other end of the dowel 458. The pull reel 455 also shows and optional notch 457 that aids in tangential loading and alignment of the pull ribbon with the pull reel 455. In this example embodiment, the pull gear 445 and the push gear 440 are disposed between a first side of the gear block 439 and a first side of a handle housing 438, while the thumbwheel push reel 450 and the pull reel 455 are disposed between a second side of the gear block 439 and a second side of a handle housing 437.

Figure 4B:
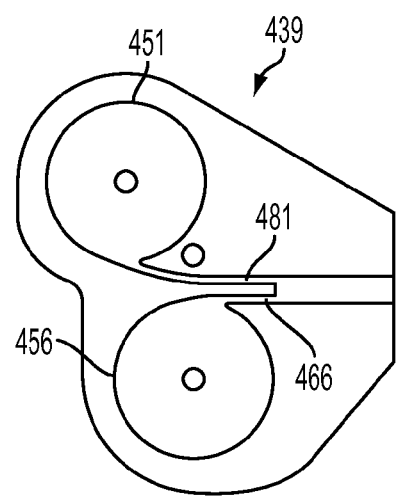
FIG. 4B is a side view of the gear box shown in FIG. 4A.
Figure 5B:
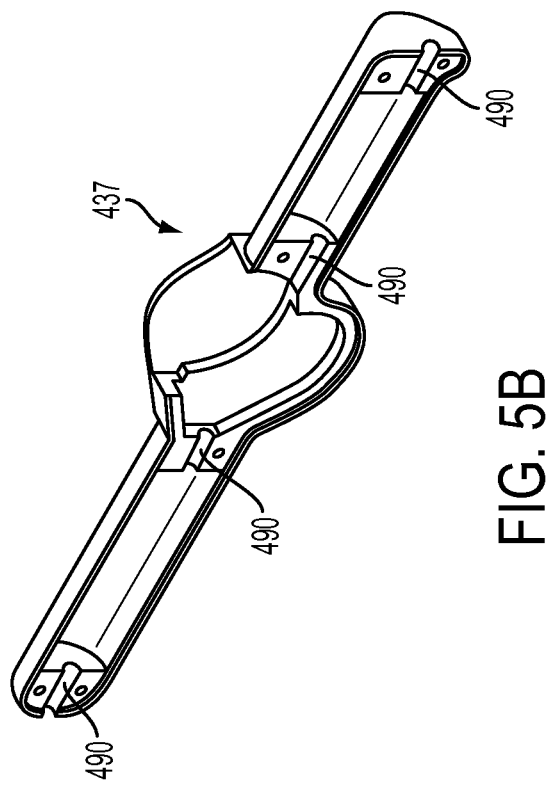
FIG. 5B is an isometric view of the inward face of a second side of the handle housing for the push-pull drive mechanism shown in FIG. 4A.
Figure 5A:
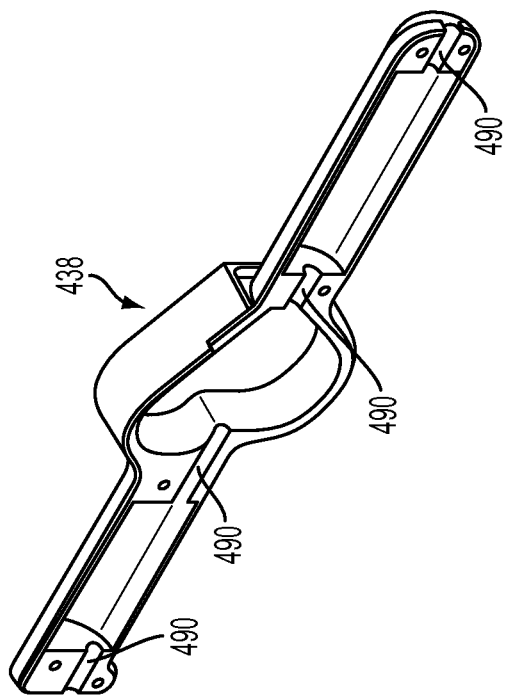
FIG. 5A is an isometric view of the inward face of a first side of the handle housing for the push-pull drive mechanism shown in FIG. 4A.

As shown in FIG. 4B, in this example embodiment, cavities 451, 456 are defined within the gear block 439 and are designed to receive the push reel and the pull reel, respectively. The gear block further defines push ribbon channel 481 and pull ribbon channel 466 to help guide the push and pull ribbons onto and off of their respective reels. In addition, the gear block defines a central core 490 between the push ribbon channel 481 and the pull ribbon channel 456 in order to receive guidewire 491. This guidewire central core 490 likewise extends through the handle housing 437, 438, as shown in FIGS. 5A-B, and to the outer sheath.

In another embodiment, not shown, the invention provides that the push-pull drive mechanism comprises: (a) the pull reel, (b) the push reel, where the push reel and the pull reel are sized and shaped based on the stent ratio, and (c) a drive gear, where the pull reel, the push reel and the drive gear are coupled together along a shared axis. In various embodiments, the pull reel, the push reel and the drive gear are mounted on a single axle. In one embodiment, the pull reel and the push reel may be mounted on opposing sides of the drive gear. In one embodiment, a drive gear, the push reel and the pull reel are coupled together along a shared axis with facial contact and rotatably mounted within a housing for the push-pull mechanism. In another embodiment, the drive gear, the push reel and the pull reel are statically mounted on a single axle either with facial contact or in an adjacent but spaced apart configuration, where the axle's ends are fixed between opposing sides of a housing for the push-pull-mechanism. This allows the push ribbon and the pull ribbon to wind and unwind with minimal resistance. In another embodiment, the pull reel may be mounted in between the drive gear and the push reel. In a further embodiment, the push reel may be mounted in between the drive gear and the pull reel. The push reel and the pull reel are sized based on the stent ratio.

Figure 6A:
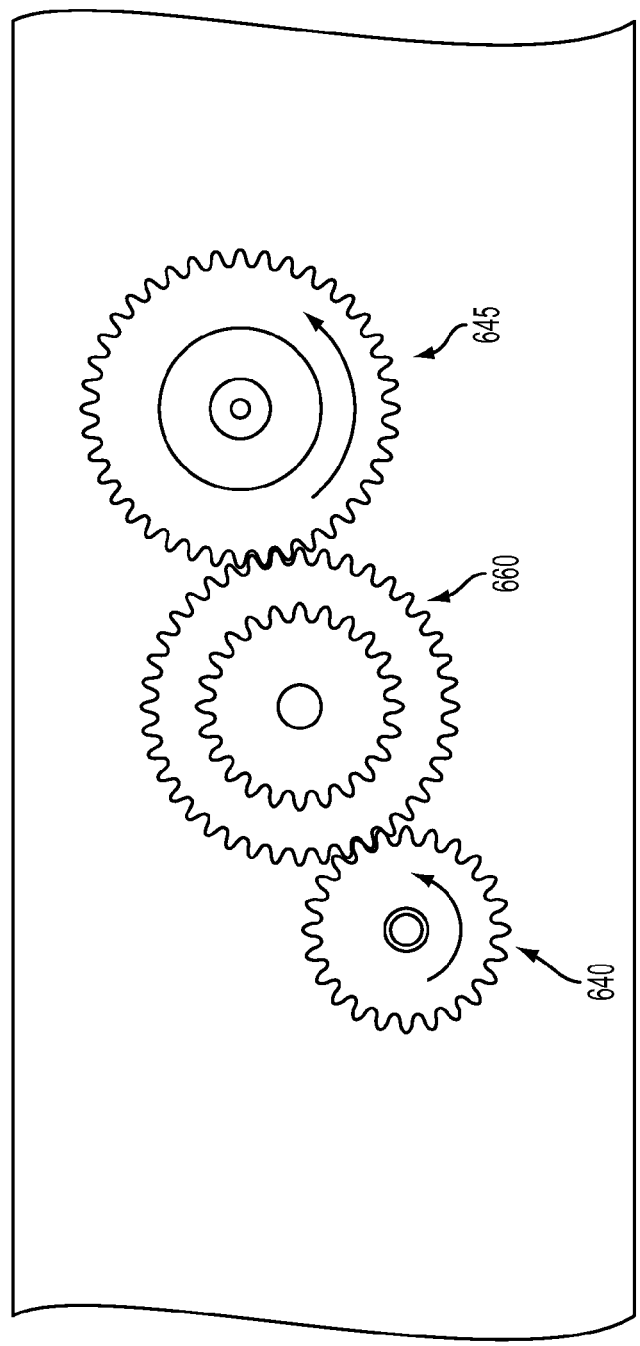
FIG. 6A is a side view of a portion of the push-pull drive mechanism according to a rack and pinion embodiment of the invention.
Figure 6B:
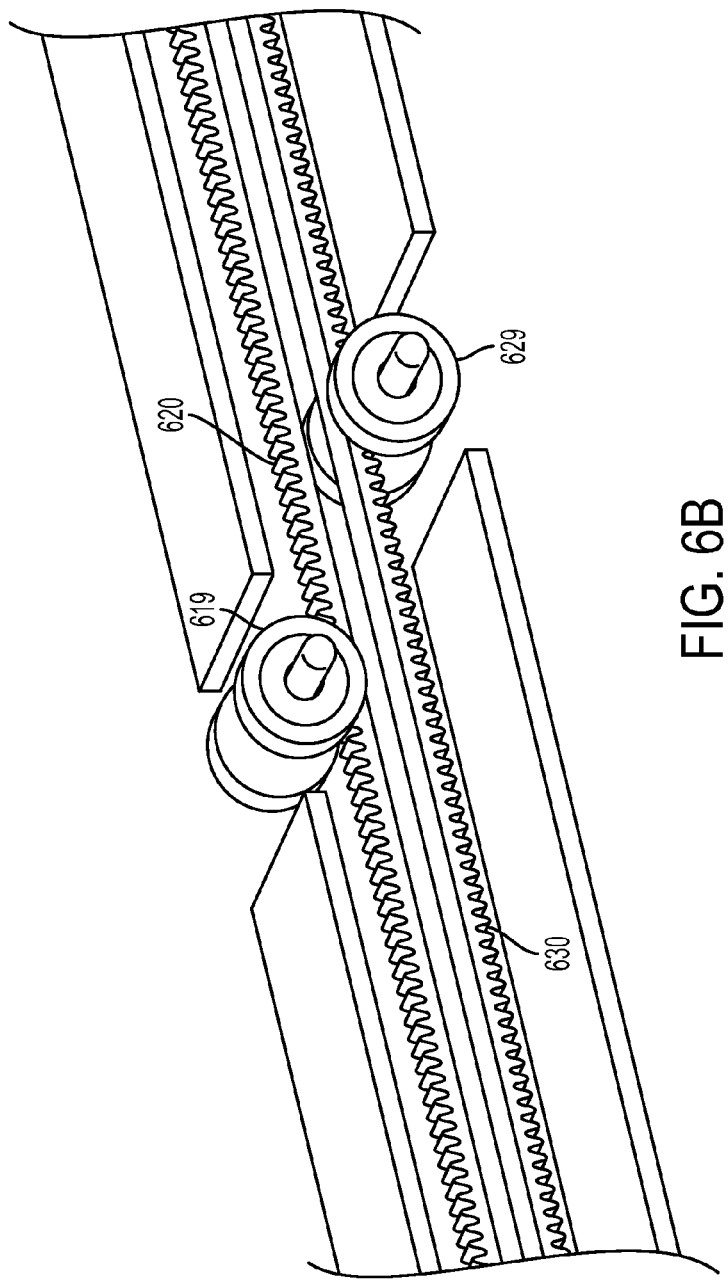
FIG. 6B is an isometric view of a portion of the push-pull drive mechanism according to a rack and pinion embodiment of the invention.

In still a further embodiment shown in FIGS. 6A-B, the invention provides that the push-pull drive mechanism 635 comprises: (a) a push apparatus that comprises a push rack 630 that defines a plurality of teeth, (b) a push pinion 629 engaged with at least one tooth of the plurality of teeth of the push rack 630, (c) the push gear 640 coupled to the push pinion 629, (d) a pull apparatus that comprises a pull rack 620 that defines a plurality of teeth, (e) a pull pinion 619 engaged with at least one tooth of the plurality of teeth of the pull rack 620, (f) the pull gear 645 coupled to the pull pinion 619, and (g) a drive gear 660 coupled to both the push gear 640 and the pull gear 645, where the push gear 640 and the pull gear 645 are sized and shaped based on the stent ratio.

This rack and pinion system converts rotational motion from the pull gear 645 and push gear 640 into linear motion. The push pinion 629 and the pull pinion 619 are circular gears that engage teeth on linear "gear" bars, here the push rack 630 and pull rack 620; rotational motion applied to the pinions causes the racks to move, thereby translating the rotational motion of the pinions into the linear motion of the racks. In one embodiment, the teeth on the push rack 630 and the teeth on the pull rack 620 face away from each other when the push rack 630 and pull rack 620 are adjacent one another, but when the push pinion 629 and pull pinion 619 are placed in between the push rack 630 and the pull rack 620, then the teeth on the push rack 630 face the teeth on the pull rack 620. A drive gear 660 is coupled to both the push gear 640 and the pull gear 645 such that when the drive gear 660 is driven by hand or by motor, the push gear 640 and the pull gear 645 turn in the same direction, but the orientation of the push rack 630 and pull rack 620 relative to the pinions 619, 629 cause the push rack 630 to be advanced forward and the pull rack 620 to be retracted. The push gear 640 and the pull gear 645 are sized based on the stent ratio.

In a combination of both a rack and pinion and push-pull coil systems, not shown, a pull reel is coupled to the proximal end of the pull apparatus. The pull apparatus comprises a ribbon at the proximal end that transitions to a pull shaft and the pull shaft then transitions to a pull tube at the distal end. In this example embodiment, the pull ribbon defines a plurality of teeth on one side and the pull gear is engaged with at least one tooth of the plurality of teeth of the pull ribbon. The push reel is likewise coupled to the proximal end of the push apparatus. The push apparatus comprises a ribbon at the proximal end that transitions to a push shaft at the distal end. In this embodiment, the push ribbon defines a plurality of teeth on one side and the push gear is engaged with at least one tooth of the plurality of teeth of the push ribbon. The push reel and the pull reel are each mounted on a rotating axle, where each axle's ends are fixed between opposing sides of a housing for the push-pull mechanism, to allow the push ribbon and the pull ribbon to wind and unwind with minimal resistance. In one preferred embodiment, the pull reel and the push reel are mounted distal to the pull gear and push gear, respectively.

In one embodiment, the pull ribbon and the push ribbon are each guided through a channel in the outer sheath. In one embodiment, this channel may be shared by the push and pull ribbons. In another embodiment, there may be a channel for each of the pull ribbon and the push ribbon. In each embodiment, the guiding channel(s) should be narrow to prevent kinking of the push and pull ribbons. Further, the pull ribbon and the push ribbon may each have a cross-section of any shape, for example, rectangular, square, round, hexagonal etc., and may further take the form of a wire.

In a ratcheting push-pull coil system, shown in FIGS. 7A-D, a pull reel is coupled to the proximal end of the pull apparatus. The pull apparatus comprises a ribbon at the proximal end that transitions to a pull shaft and the pull shaft then transitions to a pull tube 775 at the distal end 723 of the pull apparatus. In this embodiment, the pull tube 775 defines a plurality of teeth 776 along at least a portion of an inner wall of the pull tube 775. The plurality of teeth 776 on the pull tube 775 are uniform but asymmetrical, such that each tooth has a first slope on a first edge 777 and a second slope on a second edge 778, where the second slope is greater than the first slope. In some embodiments, the first slope can range from about 1/100 to 1 and the second slope can range from about 1.5 to about infinity. In a preferred embodiment, the second edge 778 is vertical, providing a slope of infinity for the second slope or, put another way, the second edge 778 is ninety degrees from the inner wall of the pull tube 775. In some embodiments, the first edge 777 and the second edge 778 meet in an apex and, in various other embodiments, as shown in FIGS. 7A-D, each tooth has a blunt finish. In one embodiment, the plurality of teeth 776 are defined in at least one track extending between the distal end 723 and proximal end of the pull tube 775. In a preferred embodiment, at least two tracks of teeth are defined on opposing sides of the inner wall of the pull tube 775. In another embodiment, the plurality of teeth are annular such that each tooth spans 360 degrees of the inner wall and the plurality of teeth extend along at least a portion of the length of the pull tube 775. In a further embodiment, the pull tube 775 comprises a slit along the length of the pull tube 775. In an embodiment in which the pull tube 775 is injection molded, the slit aids in the manufacturing process by allowing an internal mold for the teeth to be removed from the pull tube after the material has cured.

A push reel is likewise coupled to the proximal end of the push apparatus. The push apparatus comprises a ribbon at the proximal end that transitions to a push shaft 785 at the distal end 733. A stopper wedge 786 is attached to the distal end 733 of the push shaft 785 to prevent the pull apparatus from moving distally and stretching out the stent 725 after the pull apparatus has been advanced proximally. Specifically, the stopper wedge 786 is configured to have a sloped outer surface 787 and a central core 788 adapted to receive a guidewire 791. The outer surface 787 of the stopper wedge 786 is sized and shaped to fit into the depressions between the teeth lining the inner surface of the pull tube 775. The slope of the stopper wedge's outer surface 787 preferably matches the first slope of the teeth 776 on the pull tube 775, such that the first edge 777 of a respective tooth slides over the surface 787 of the stopper wedge 786 as the pull tube 775 is moved in an unrestricted (i.e., proximal) direction. The pull tube teeth 776 and/or the stopper wedge 786 are constructed from a resilient but flexible material that allows flexure when the apex of the pull tube teeth 776 advance toward and meet the proximal edge 789 of the stopper wedge's outer surface allowing a tooth 776 to move proximal to the stopper wedge 786. If the device attempts to move the pull tube teeth 776 in the opposite (i.e., distal) direction, the stopper wedge 786 catches against the second edge 778 of the first tooth it encounters, thereby locking the stopper wedge 786 against the respective tooth and preventing any further movement in that direction.

FIG. 7A shows the push shaft 785 and the stopper wedge 786 disposed adjacent the proximal end of the constrained stent 725 at a first time T1 prior to deployment. At time T1, the constrained stent 725 is disposed within the pull tube 775, while the pull tube 775 is disposed within an outer sheath 715. FIG. 7B shows the stent deployment device at a second time T2 with the outer sheath 715 partially retracted from the pull tube 775. FIG. 7C shows the stent deployment device at a third time T3 with the stopper wedge 786 displaced distally within the pull tube 775 and the stent 725 partially deployed. FIG. 7D shows the stent deployment device at a fourth time T4 with the stent 725 fully deployed and the stopper wedge 786 displaced to the distal end 723 of the pull tube 775.

In an alternative embodiment, shown in FIG. 8, the guidewire core 890 may be off-center and adjacent to the pull apparatus and the push apparatus within the outer sheath. In this embodiment, the outer sheath acts as a three-tube manifold 815. The outer sheath 815 may be heat shrunk around three stainless steel hypodermic tubes to create three lumens. One lumen 890 receives a guidewire 891, another lumen receives a push wire 830 and the remaining lumen receives a pull wire 820. In one embodiment the three-tube manifold is about 2.5 inches long and comprises a stiff polymer tube that is ⅜ inches in diameter. The three-tube manifold transitions into a length of unsupported wire and the stiff nature of the outer sheath minimizes kinking during stent deployment. The length of the unsupported wire should be slightly longer than the distance of travel of the pull tube 875 to prevent the pull tube 875 from bottoming out against the three-tube manifold. In one embodiment, the push wire is pinch fit into the push wire lumen with an overlap of approximately 2 inches.

In example embodiments, the push ribbon and pull ribbon may comprise a nitinol wire or braided stainless steel. The push ribbon 880 and the pull ribbon 865 move through a drilled out and capped channel that ultimately transitions into separate laser cut channels, for example. These channels terminate at the distal end of the push-pull drive mechanism. From there, the push ribbon 880 and the pull ribbon 865 pass through a three-tube manifold, as described above, which are heat shrunk together, for example, in a non-concentric manner. The push ribbon 880 and pull ribbon 865 pass through a separate hypotube (e.g., the guide wire lumen, the push ribbon lumen, pull ribbon lumen). The foregoing system provides support and guidance for the wires.

In alternative arrangements, the three-tube manifold may comprise a continuous stainless steel hypotube that originates from either of its respective reels or a guide wire luer lock. This flexible hypotube fits into a machined groove in the outer handle, for example. The groove acts as a guide that holds the hypotube in place. In the case of the push ribbon 880 and pull ribbon 865, this continuous hypotube has the advantage of continuously supporting the push ribbon 880 in the push segment and the pull ribbon 865 in the pull segment. In the case of the guide wire supporting lumen 890, the continuous tubing has the advantage of providing fluid management for water/lubricants added from the luer lock while minimizing the number of transitions and gaskets needed. This approach has an added benefit in that it minimizes the amount of expensive, high-precision laser cut through holes. In an example embodiment, the pull ribbon 865 transitions directly into a pull tube 875.

In this example, the pull ribbon 865 may be secured to the pull tube 875 with heat shrink, the push ribbon 880 is pinch fit into one of the lumens of a two-lumen balloon that acts as the push shaft 885, and the guide wire 891 passes freely through the guide wire lumen 890 of the two-lumen balloon. Alternatively, a plurality of wires extend from the proximal end of the pull tube; some of the plurality of wires may be cut and the remainder braided into a single cable. For example, in one embodiment, the pull tube is made from a polymer sheath that has 16 wires connected around the sheath's periphery, for example. These wires are woven to act as the pull ribbon and to add strength and rigidity to the pull apparatus. And, in some example embodiments, twelve (12) of the sixteen (16) wires will be cut at the proximal end of the pull tube, while the remaining four (4) connected wires are braided together to form the pull apparatus. In another example, the pull wire could be solid bonded to the pull tube.

The push shaft could be manufactured in a number of ways. One is through a wire braiding process similar to the pull apparatus. Another embodiment is through solid bonding to the push shaft. A third example embodiment is a coiled wire defining an inner lumen. This coiled wire transitions to an uncoiled straight segment where the guide wire enters on the proximal end of the coil. The coil then continues through the distal end of the push apparatus, allowing the guide wire to pass through.

All embodiments of the stent deployment device 10 of the invention can be used in the methods of the second aspect of the invention. Note that any of the foregoing embodiments of any aspect may be combined together to practice the claimed invention.

The invention claimed is:

1. A stent deployment device, comprising:
an outer sheath, wherein the outer sheath has a proximal end and a distal end, wherein a portion of the outer sheath defines a central core;
a pull apparatus at least partially disposed within the outer sheath, wherein a portion of the pull apparatus is sized and shaped to receive a stent or a stent graft, wherein a proximal end of the pull apparatus comprises a pull ribbon that transitions to a pull shaft and the pull shaft then transitions to a pull tube at a distal end of the pull apparatus;
a push apparatus, wherein a proximal end of the push apparatus comprises a push ribbon that transitions to a push shaft at a distal end of the push apparatus, wherein a portion of the push shaft is disposed within the pull tube, wherein the push shaft defines a central core, wherein the pull shaft defines both a central core and a channel in which the push ribbon is disposed, and wherein the central core of the outer sheath, the central core of the pull shaft and the central core of the push shaft are all aligned in series and configured to receive a guidewire; and
a push-pull drive mechanism in mechanical communication with the pull apparatus and the push apparatus, wherein the push-pull drive mechanism comprises a pull reel and a push reel, wherein the pull reel is directly coupled to the pull ribbon such that at least a portion of the pull ribbon is configured to wrap around the pull reel, and wherein the push reel is directly coupled to the push ribbon such that at least a portion of the push ribbon is configured to wrap around the push reel.

2. The stent deployment device of claim 1, wherein the push-pull drive mechanism further comprises:
a pull gear in mechanical communication with the pull reel;
a push gear in mechanical communication with the push reel; and
a drive gear in mechanical communication with the push gear and the pull gear, wherein the push gear and the pull gear are sized and shaped based on a stent ratio.

3. The stent deployment device of claim 2, wherein the push gear is smaller than the pull gear.

4. The stent deployment device of claim 2, wherein the drive gear is coupled to a motor.

5. The stent deployment device of claim 2, wherein the drive gear is coupled to a manual override.

6. The stent deployment device of claim 5, wherein the manual override comprises a thumb wheel.

7. The stent deployment device of claim 2, wherein the drive gear is configured to be manually turned by hand.

8. The stent deployment device of claim 1, wherein the push-pull drive mechanism further comprises:
a drive gear, wherein the pull reel, the push reel and the drive gear are coupled together along a shared axis, and wherein the push reel and the pull reel are sized and shaped based on a stent ratio.

9. The stent deployment device of claim 8, wherein the push reel is larger than the pull reel.

10. The stent deployment device of claim 1, wherein the push-pull drive mechanism further comprises:
a drive gear, wherein the pull reel, the push reel and the drive gear are mounted on a single axle, and wherein the push reel and the pull reel are sized and shaped based on a stent ratio.

11. The stent deployment device of claim 1, wherein the pull tube comprises a slit along the length of the pull tube.

12. The stent deployment device of claim 1, wherein a portion of the outer sheath defines a channel for receiving the pull ribbon and a channel for receiving the push ribbon.

13. The stent deployment device of claim 1, further comprising a guidewire disposed within the central core of the outer sheath, the central core of the pull shaft and the central core of the push shaft.

14. The stent deployment device of claim 1, further comprising a stent restraint coupled to a distal end of the push shaft.

15. The stent deployment device of claim 14, wherein the stent restraint comprises two wires with inward facing hooked ends extending from the distal end of the push shaft and outwardly biased towards the pull tube.

16. The stent deployment device of claim 1, further comprising a push gear and a pull gear that are sized and shaped based on a stent ratio, wherein a ratio of a diameter of the pull gear to a diameter of the push gear is equal to the stent ratio plus 5-15% of the stent ratio.

17. The stent deployment device of claim 16, wherein the ratio of the diameter of the pull gear to the diameter of the push gear is equal to the stent ratio plus 10% of the stent ratio.

18. The stent deployment device of claim 1, wherein the push reel and the pull reel are sized and shaped based on a stent ratio, wherein a ratio of a diameter of the push reel to a diameter of the pull reel is equal to the stent ratio plus 5-15% of the stent ratio.

19. The stent deployment device of claim 18, wherein the ratio of the push reel diameter to the pull reel diameter is equal to the stent ratio plus 10% of the stent ratio.

20. The stent deployment device of further comprising a pull gear and a push gear, claim 1, wherein a ratio of a diameter of the pull gear to a diameter of the push gear is equal to a stent ratio.

21. The stent deployment device of claim 1, wherein the push reel and the pull reel are sized and shaped based on a stent ratio, wherein a ratio of a diameter of the push reel to a diameter of the pull reel is equal to the stent ratio.

22. A method for placement of a stent graft, the method comprising: providing the stent deployment device of claim 1;
simultaneously advancing a stent or a stent graft distally with the push apparatus of the stent deployment device and retracting the pull apparatus of the stent deployment device proximally at two different rates based on a stent ratio; and
deploying the stent or the stent graft into a lumen.

23. The method of claim 22, further comprising the step of recapturing the stent or the stent graft by using a stent restraint in communication with an end of the stent or the stent graft.

* * * * *